(12) United States Patent
Norton et al.

(10) Patent No.: US 10,485,532 B2
(45) Date of Patent: Nov. 26, 2019

(54) SUTURE PASSER DEVICE INCLUDING A BLUNT TIP AND A SHARP TIP

(71) Applicant: Biomet Manufacturing, LLC, Warsaw, IN (US)

(72) Inventors: Daniel Norton, Winona Lake, IN (US); Kevin T. Stone, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 452 days.

(21) Appl. No.: 14/041,305

(22) Filed: Sep. 30, 2013

(65) Prior Publication Data
US 2015/0094739 A1    Apr. 2, 2015

(51) Int. Cl.
*A61B 17/04* (2006.01)
*A61B 17/06* (2006.01)

(52) U.S. Cl.
CPC ...... *A61B 17/0469* (2013.01); *A61B 17/0401* (2013.01); *A61B 17/0482* (2013.01); *A61B 17/0483* (2013.01); *A61B 2017/044* (2013.01); *A61B 2017/0414* (2013.01); *A61B 2017/06042* (2013.01); *A61B 2017/06052* (2013.01)

(58) Field of Classification Search
CPC ............ A61B 17/0469; A61B 17/0482; A61B 17/0483; A61B 2017/06052; A61B 2017/0414; A61B 2017/06042; A61B 2017/00367; A61B 2017/00371
See application file for complete search history.

(56) References Cited

U.S. PATENT DOCUMENTS

| 5,085,661 | A | * | 2/1992 | Moss | A61B 17/0401 606/139 |
| 5,281,237 | A | | 1/1994 | Gimpelson | |
| 5,439,467 | A | * | 8/1995 | Benderev | A61B 17/0401 606/139 |
| 5,499,991 | A | * | 3/1996 | Garman | A61B 17/0483 606/148 |
| 5,562,683 | A | | 10/1996 | Chan | |
| 5,562,687 | A | | 10/1996 | Chan | |
| 5,676,675 | A | | 10/1997 | Grice | |
| 5,776,151 | A | | 7/1998 | Chan | |
| 5,817,111 | A | * | 10/1998 | Riza | A61B 17/0483 112/169 |
| 5,904,692 | A | * | 5/1999 | Steckel | A61B 17/0469 128/898 |
| 6,102,920 | A | * | 8/2000 | Sullivan | A61B 17/062 606/147 |
| 6,629,984 | B1 | | 10/2003 | Chan | |

(Continued)

*Primary Examiner* — Ryan J. Severson
*Assistant Examiner* — Christian D Knauss
(74) *Attorney, Agent, or Firm* — Schwegman Lundberg & Woessner, P.A.

(57) ABSTRACT

The present disclosure describes a suture passer device that includes a handle, a shaft extending from the handle, and a suture carrier secured to the handle and moveable through a distal end of the shaft. According to one aspect of the present disclosure, one of the shaft and the suture carrier includes a sharp tip and the other one of the shaft and the suture carrier includes a blunt tip. According to another aspect of the present disclosure, the suture carrier includes an inner tube extending through the shaft and a flexible arm extending through the inner tube. Methods of using a suture passer device are also disclosed.

10 Claims, 9 Drawing Sheets

(56) References Cited

U.S. PATENT DOCUMENTS

| | | | |
|---|---|---|---|
| 6,893,448 B2* | 5/2005 | O'Quinn | A61B 17/0469 606/139 |
| 2007/0038230 A1* | 2/2007 | Stone | A61B 17/0482 606/139 |
| 2009/0018554 A1* | 1/2009 | Thorne | A61B 17/0485 606/145 |
| 2011/0071551 A1* | 3/2011 | Singhatat | A61B 17/0401 606/145 |
| 2012/0123448 A1* | 5/2012 | Flom | A61B 17/0469 606/144 |
| 2012/0143224 A1 | 6/2012 | Chan | |
| 2013/0116710 A1 | 5/2013 | Ziniti et al. | |

* cited by examiner

SUTURE PASSER DEVICE INCLUDING A BLUNT TIP AND A SHARP TIP

FIELD

The present disclosure relates to suture passer devices, and more particularly, to suture passer devices including a blunt tip and a sharp tip.

BACKGROUND

This section provides background information related to the present disclosure which is not necessarily prior art.

Various devices and methods are known for suturing soft tissue in connection with arthroscopic, endoscopic, or other surgical procedures. These and other small-incision or less invasive surgical procedures generally require that suturing and the associated manipulation of suturing are performed in confined areas which are not easily accessible.

Although the existing devices can be satisfactory for their intended purposes, there is still a need for procedures and devices that provide greater control in the passage of sutures, greater control in the passage of delicate sutures, and increased flexibility in the types and thicknesses of tissues that can be sutured in ordinary and in less invasive procedures.

SUMMARY

This section provides a general summary of the disclosure, and is not a comprehensive disclosure of its full scope or all of its features.

The present disclosure describes a suture passer device that includes a handle, a shaft extending from the handle, and a suture carrier secured to the handle and moveable through a distal end of the shaft. According to one aspect of the present disclosure, one of the shaft and the suture carrier includes a sharp tip and the other one of the shaft and the suture carrier includes a blunt tip. According to another aspect of the present disclosure, the suture carrier includes an inner tube extending through the shaft and a flexible arm extending through the inner tube. Methods of using a suture passer device are also disclosed.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Suture passer devices can be used to pass a suture around soft tissue or through soft tissue. Typically, a suture passer device either has a sharp tip to pierce a hole in soft tissue or a blunt tip to avoid damaging the soft tissue. However, a suture passer device according to the principles of the present disclosure can be transformed from having a blunt tip to have a sharp tip and vice versa. Thus, the suture passer device can be used to pass a suture around soft tissue without damaging the soft tissue and to pass a suture through soft tissue by piercing a hole in the soft tissue.

In one example, a suture passer device according to the principles of the present disclosure includes an outer tube or shaft and an inner tube that can be extended out of the outer tube and retracted into the outer tube. The outer tube can have a blunt tip and the inner tube can have a sharp tip so that extending the inner tube out of the outer tube transforms the suture passer device from having a blunt tip to having a sharp tip. Alternatively, the inner tube can have a blunt tip and the outer tube can have a sharp tip so that extending the inner tube out of the outer tube transforms the suture passer device from having a sharp tip to having a blunt tip.

In another example, the inner tube can define a notch or opening adjacent to its distal end for retaining a suture. In addition, the suture passer device can include a flexible arm that can be extended through the opening in the inner tube to grab a suture using, for example, a notch defined in the flexible arm adjacent to its distal end. The flexible arm can then be retracted into the inner tube to fix the suture within the inner tube.

Referring now to FIGS. 1A, 1B, 2A, 2B, 3A, 3B, 4A, and 4B, a suture passer device 10 has a longitudinal axis x and includes a handle assembly 12, an outer shaft or tube 14, an inner tube 16, and an elongated suture passer or flexible arm 18. The handle assembly 12 includes a handle 20, a trigger 22 that is pivotally coupled to the handle 20, and a slide button 24 that is slidably coupled to the handle 20 to slide axially relative to the handle 20. The handle 20 has a proximal end 26 and a distal end 28, and indentations or grooves 30 configured to nestingly engage fingers of a user when the user grips the handle 20. The handle 20 can be made from plastic or other materials known in the art.

The outer tube 14 extends from the handle 20 along the longitudinal axis X and has a proximal end 32 and a distal end or tip 34. The proximal end 32 of the outer tube 14 can be fixed to the distal end 28 of the handle 20 using, for example, a press or interference fit, a threaded connection, and/or adhesive. The distal tip 34 of the outer tube 14 can be blunt (e.g., flat, rounded), as shown, to avoid damaging tissue, or the distal tip 34 can be sharp (e.g., conical) to pierce tissue. The outer tube 14 defines a channel 36 (FIG. 2B) that extends between the proximal end 32 and the distal tip 34 and is configured to receive the inner tube 16. The outer tube 14 can also define axially extending slots 38 (only one shown) disposed on opposite sides of the outer tube 14 and extending into the distal tip 34 of the outer tube 14 along the longitudinal axis X. The slots 38 can be u-shaped, as shown, and can provide access to the inner tube 16 when the inner tube 16 is retracted into the channel 36 in the outer tube 14.

Figures 1A, 1B:
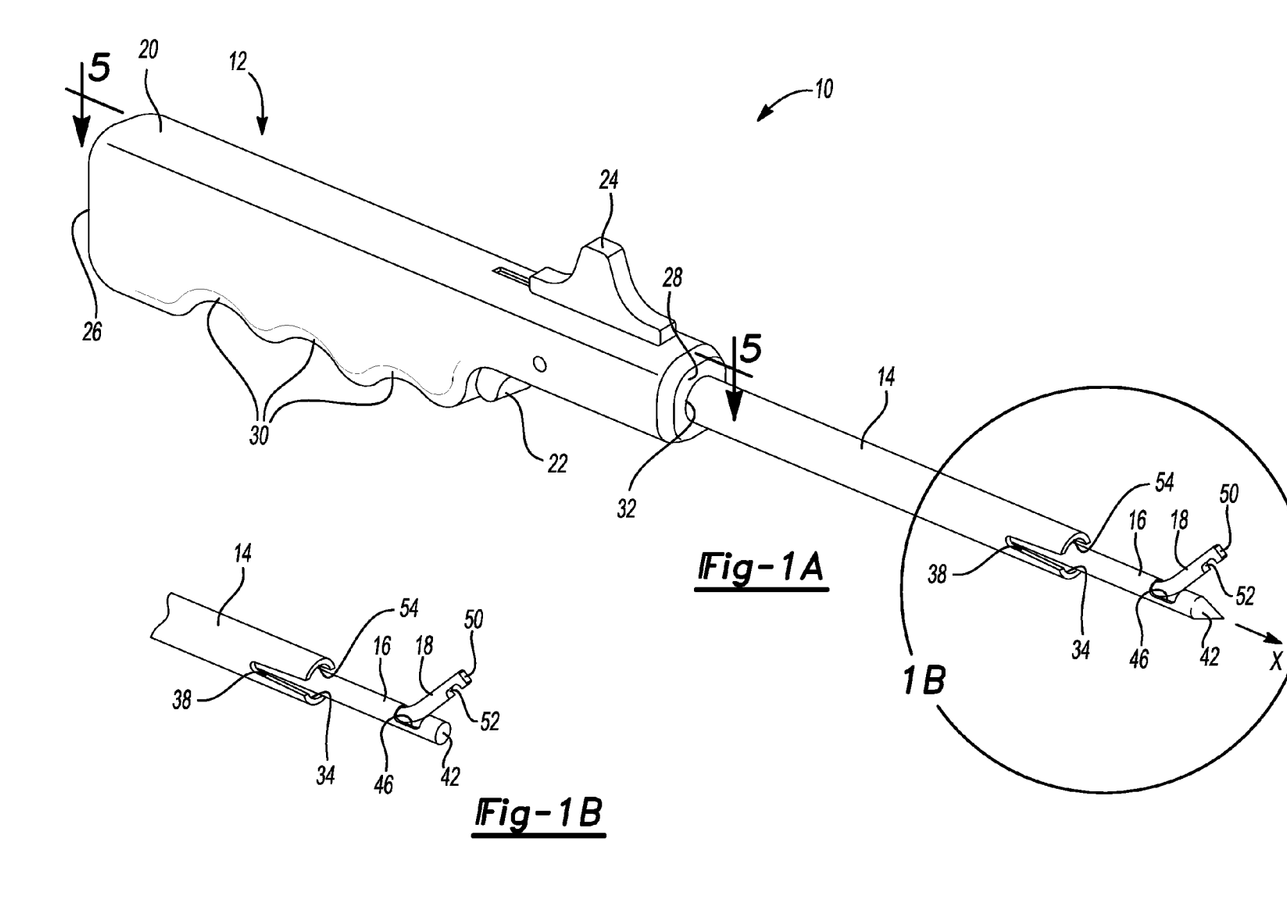
FIG. 1A is a perspective view of an example suture passer device according to the principles of the present disclosure, the suture passer device including an outer tube, an inner tube, and a flexible arm.
FIG. 1B is a perspective view of a portion of the suture passer device within a circle 1B shown in FIG. 1A showing the inner tube of the suture passer device with a blunt tip instead of a sharp tip as shown in FIG. 1A.
Figure 2A:
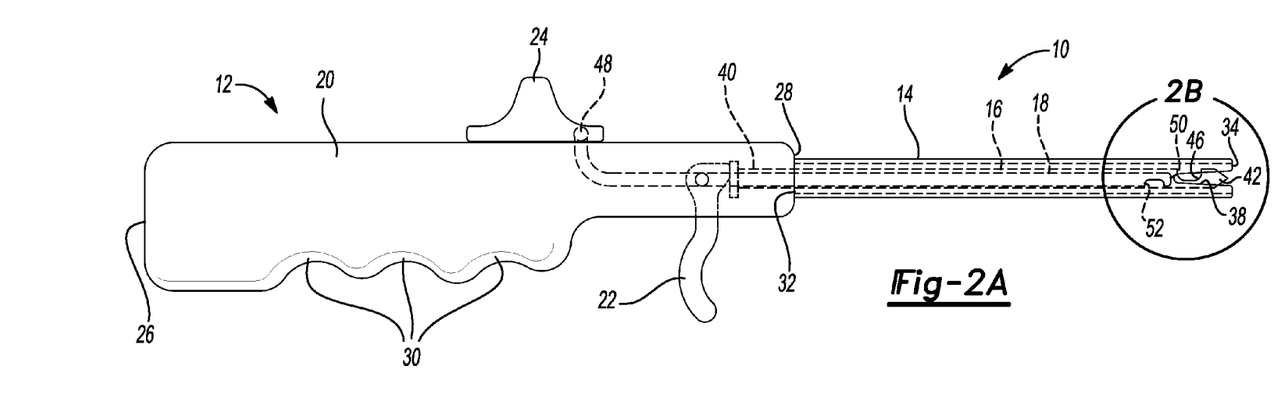
FIG. 2A is a side view of the suture passer device with the inner tube and the flexible arm in their respective retracted positions.
Figure 2B:
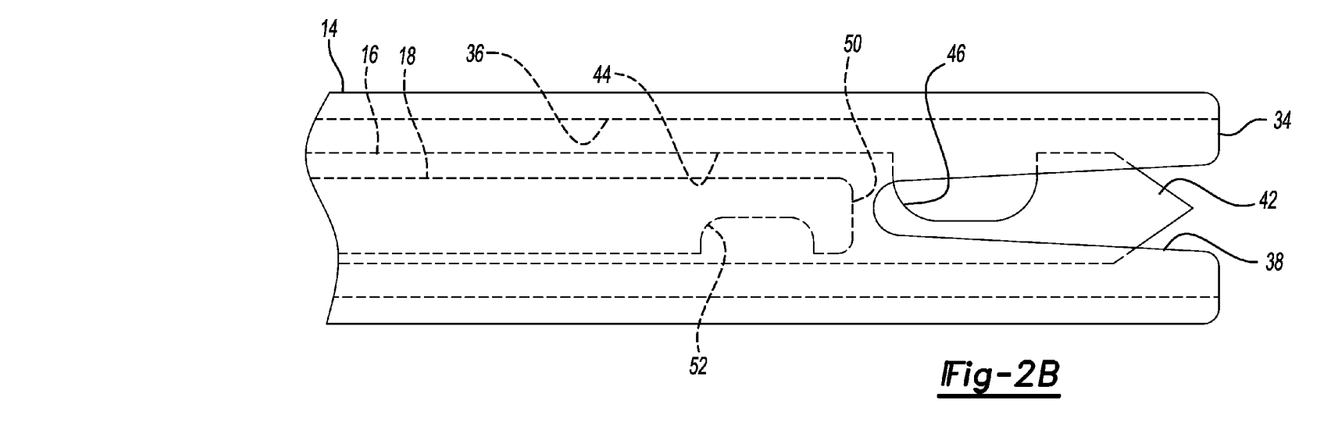
FIG. 2B is a side view of a portion of the suture passer device within a circle 2B shown in FIG. 2A.

The inner tube 16 extends through the outer tube 14 along the longitudinal axis X and has a proximal end 40 (FIG. 2A) and a distal end or tip 42. The proximal end 40 of the inner tube 16 can be captured within the handle 20 adjacent to its distal end 28, as discussed in more detail below. The distal tip 42 can be sharp (e.g., conical), as shown in FIG. 1A, for piercing tissue, or the distal tip 42 can be blunt (e.g., flat, rounded), as shown in FIG. 1B, to avoid damaging tissue. The inner tube 16 defines a channel 44 (FIG. 2B) that extends between the proximal end 40 and the distal tip 42 and is configured to receive the flexible arm 18. The inner tube 16 can define a radial opening or notch 46 adjacent to and proximal from its distal tip 42. When the inner tube 16 is retracted into the outer tube 14, the notch 46 can cooperate with the slots 38 in the outer tube 14 to form a suture eyelet configured to retain a suture. In addition, the flexible arm 18 can be extended and retracted distally and transversely or radially through the notch 46.

The outer and inner tubes 14, 16 can be cylindrical, as shown, or the outer and inner tubes 14, 16 can have another suitable shape such as rectangular cuboids. In this regard, the outer and inner tubes 14, 16 may be referred to more generally as outer and inner members, respectively. The outer and inner tubes 14, 16 can be formed from metal. In addition, although the outer and inner tubes 14, 16 are depicted as straight cylinders, in various implementations, the outer and inner tubes 14, 16 may be curved or bent.

The flexible arm 18 extends through the inner tube 16 along the longitudinal axis X and has a proximal end 48 (FIG. 2A) and a distal end or tip 50. The proximal end 48 of the flexible arm 18 can be fixed to the slide button 24, as discussed in more detail below. The distal tip 50 can be blunt, as shown, to avoid damaging tissue, or the distal tip 50 can be sharp to pierce tissue. The flexible arm 18 can be a flat strip and can be formed from a flexible material such as Nitinol or a flexible polymer. The flexible arm 18 can define a notch 52 adjacent to and proximal from its distal tip 50. The notch 52 can be rectangular or u-shaped and can extend transversely or radially through the flexible arm 18. The notch 52 in the flexible arm 18 can be used to grab a suture when the flexible arm is extended out of the inner tube 16. Since the inner tube 16 and the flexible arm 18 can each be used to carry a suture, the inner tube 16 and the flexible arm 18 can be individually or collectively referred to as a suture carrier.

Figure 3A:
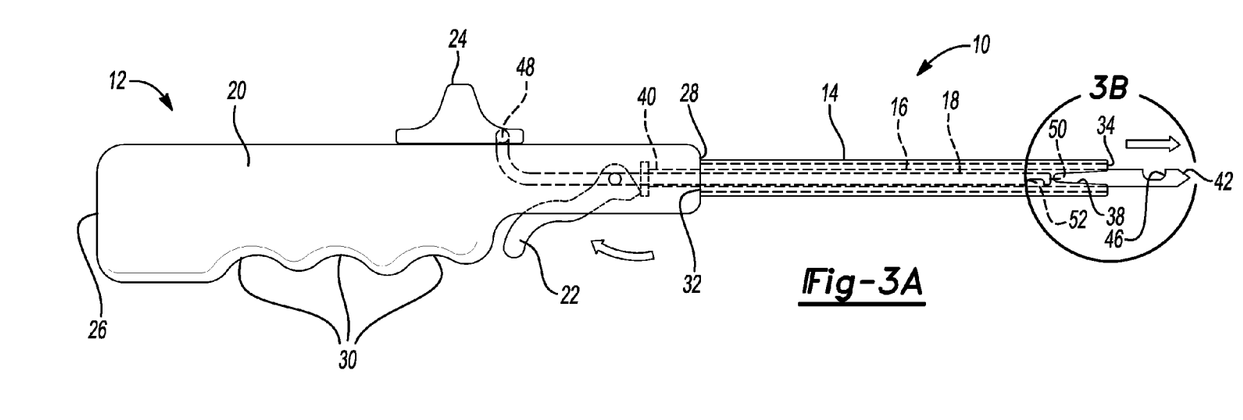
FIG. 3A is a side view of the suture passer device with the inner tube in its extended position and the flexible arm in its retracted position.
Figure 3B:
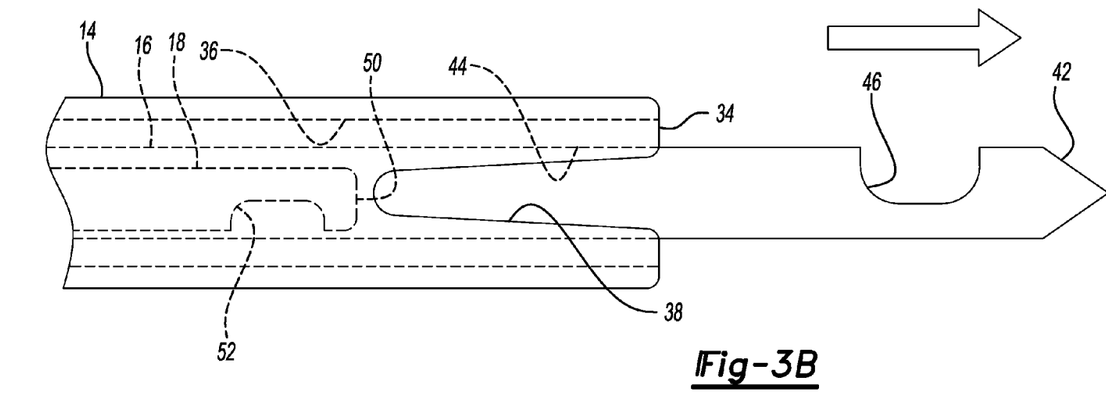
FIG. 3B is a side view of a portion of the suture passer device within a circle 3B shown in FIG. 3A.

The trigger 22 can be pulled toward the proximal end 26 of the handle 20 to actuate the inner tube 16 from its retracted position (FIG. 2A) to its axially extended position (FIG. 3A). As the inner tube 16 is actuated from its retracted position to its extended position, the inner tube 16 moves distally through an opening 54 (FIG. 1A) in the outer tube 14. In its extended position, the distal tip 42 of the inner tube 16 extends distally beyond the distal tip 34 of the outer tube 14. In this regard, extending the inner tube 16 out of the outer tube 14 exposes the distal tip 34 of the inner tube 16 and thereby transforms the suture passer device 10 from having a blunt distal tip to having a sharp distal tip.

Figure 4A:
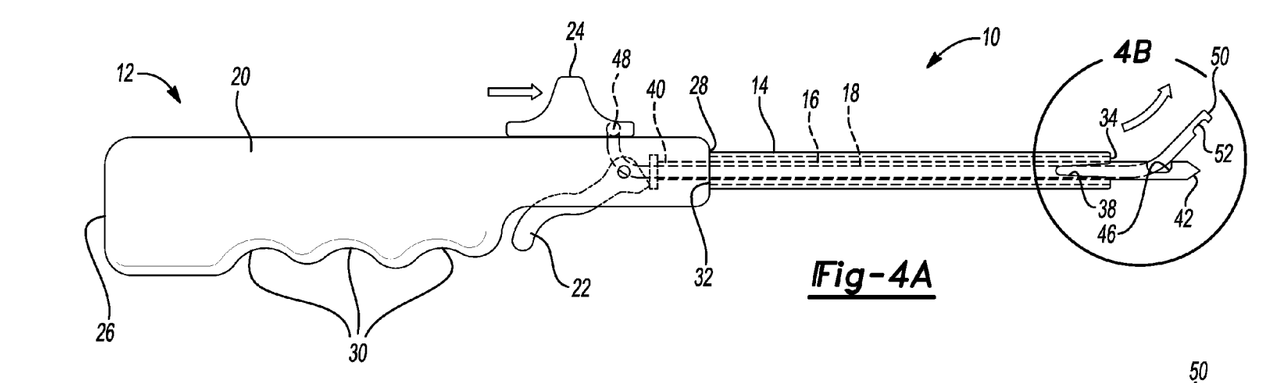
FIG. 4A is a side view of the suture passer device with the inner tube and the flexible arm in their respective extended positions.
Figure 4B:
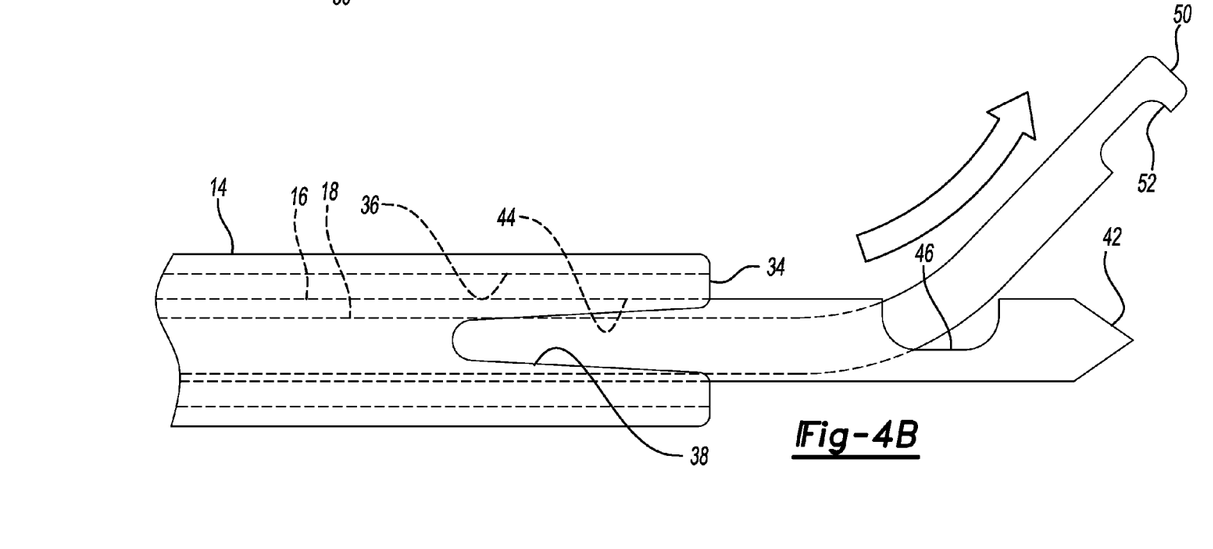
FIG. 4B is a side view of a portion of the suture passer device within a circle 4B shown in FIG. 4A.

The slide button 24 can be moved toward the distal end 28 of the handle 20 to actuate the flexible arm 18 from its retracted position (FIG. 3A) to its extended position (FIG. 4A). As the flexible arm 18 is actuated from its retracted position to its extended position, the flexible arm 18 moves distally and radially through the notch 46 in the inner tube 16. In its extended position, the distal tip 50 of the flexible arm 18 extends distally beyond the distal tip 42 of the inner tube 16 and radially away from the distal tip 42. In this regard, extending the flexible arm 18 out of the inner tube 16 exposes the notch 52 in the flexible arm 18 so that the notch 52 can be used to grab a suture.

Figure 5:
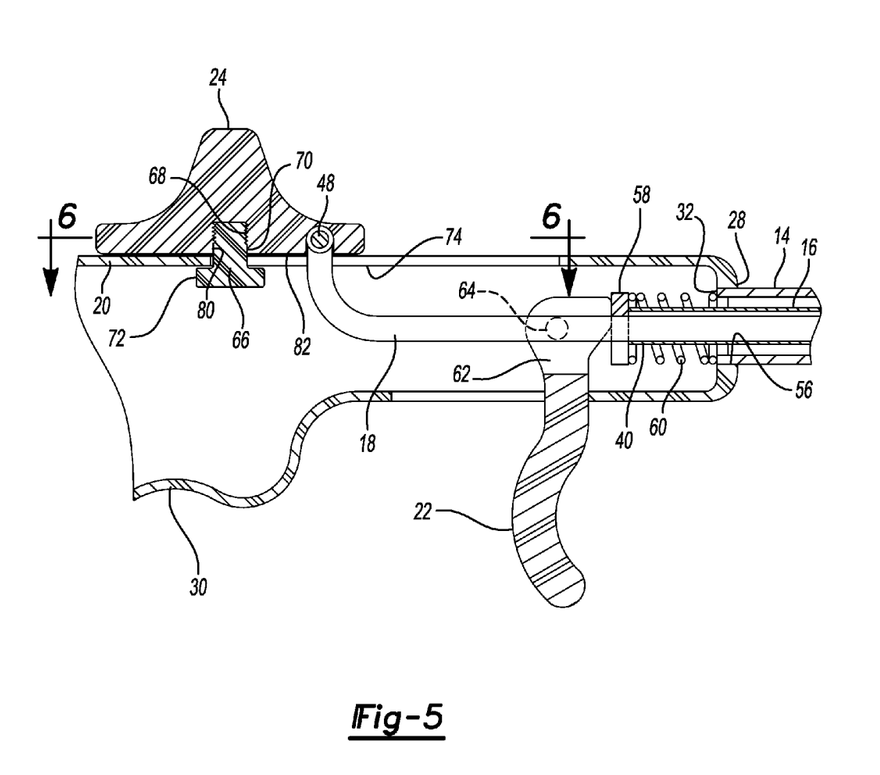
FIG. 5 is a partial section view of the suture passer device taken along a line 5-5 shown in FIG. 1A, but with the inner tube and the flexible arm in their respective retracted positions.

Referring now to FIG. 5, the proximal end 32 of the outer tube 14 can be inserted into an opening 56 in the distal end 28 of the handle 20 and secured within the opening 56 using a threaded connection, a press fit, and/or adhesive. A washer 58 can be fixed to the proximal end 40 of the inner tube 16 using a press or interference fit and/or adhesive. A coil spring 60 can be captured between the washer 58 and the proximal end 32 of the outer tube 14. The coil spring 60 biases the inner tube 16 proximally relative to the handle 20.

The trigger 22 can include a head 62 that engages the washer 58 as the trigger 22 is applied to actuate the inner tube 16 from its retracted position to its extended position. When the trigger 22 is released, the coil spring 60 moves the inner tube 16 proximally from its extended position to its retracted position. In turn, the distal tip 42 of the inner tube 16 retracts within the channel 36 in the outer tube 14, and the suture passer device 10 is thereby transformed from having a sharp distal tip to having a blunt distal tip.

The trigger 22 can be pivotally coupled to the handle 20 using a pin 64. The trigger 22 and the pin 64 can be integrally formed from, for example, plastic. Alternatively, the trigger 22 and the pin 64 can be formed separately from, for example, plastic and metal, respectively.

Figure 6:
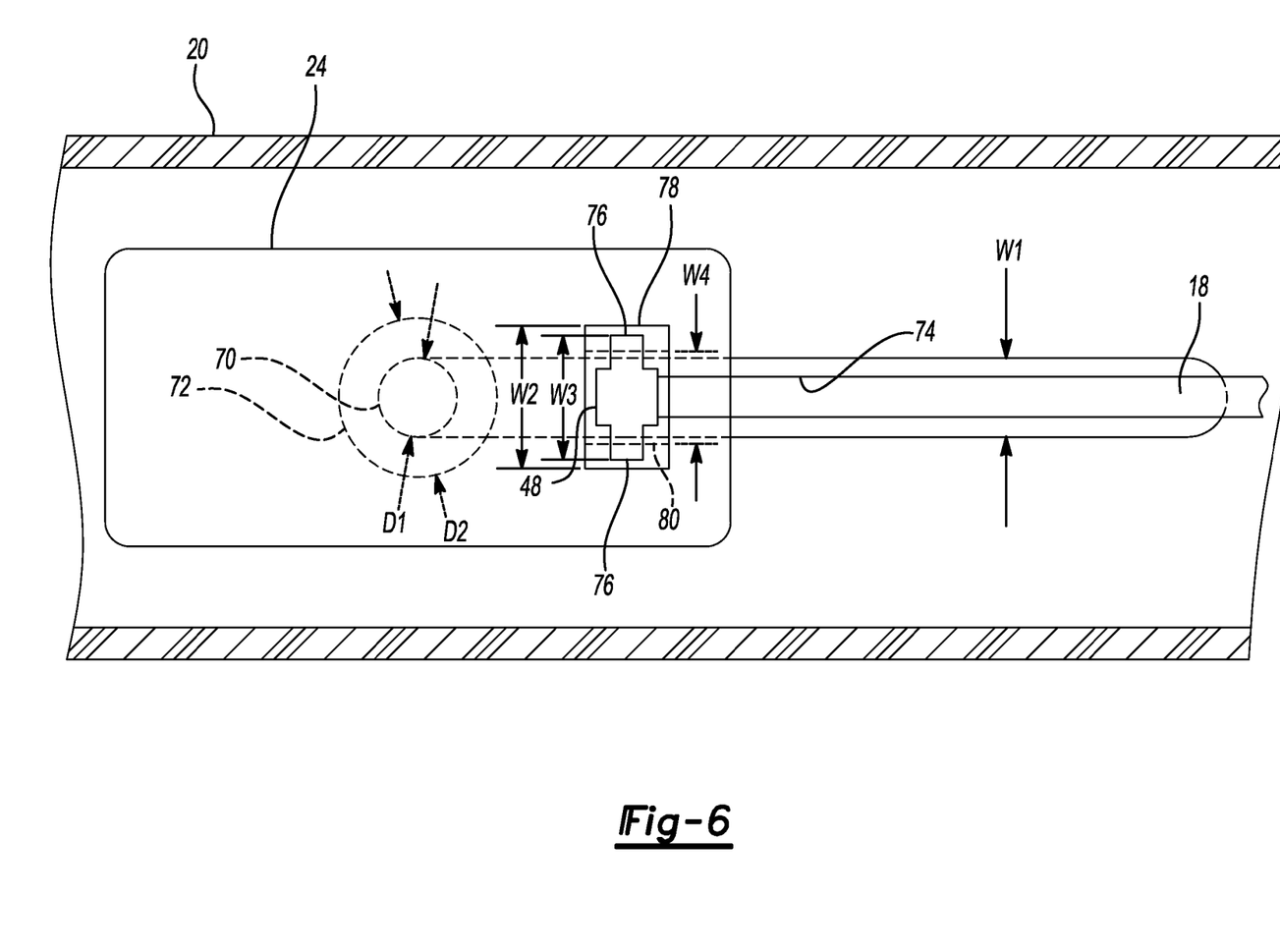
FIG. 6 is a partial section view of the suture passer device taken along a line 6-6 shown in FIG. 5.

With additional reference to FIG. 6, a fastener 66 can be threaded into a hole 68 in the slide button 24 to couple the slide button 24 to the handle 20. The fastener 66 can include a shank 70 and a head 72. The handle 20 can define a slot 74 that engages the shank 70 of the fastener 66 to guide the slide button 24 as the slide button 24 is moved axially relative to the handle 20. A width W1 of the slot 74 can be larger than a diameter D1 of the shank 70 and smaller than a diameter D2 of the head 72. Thus, after the fastener 66 is threaded into the slide button 24, the slide button 24 is secured to the handle 20 and is allowed to slide axially along the slot 74. In various implementations, the fastener 66 can be integrally formed with the slide button 24 (e.g., from plastic).

The proximal end 48 of the flexible arm 18 can include ears 76. The slide button 24 can define a pocket 78 for receiving the ears 76 and an opening 80 that extends through a bottom surface 82 of the slide button 24 to the pocket 78. A width W2 of the pocket 78 can be larger than a width W3 of the ears 76, and a width W4 of the opening 80 can be smaller than the width W3 of the ears 76. Thus, as the ears 76 are inserted through the opening 80, the ears 76 may flex inward until the ears 76 are received in the pocket 78. The ears 76 may then relax such that the ears 76 are captured within the pocket 78, thereby securing the proximal end 48 of the flexible arm 18 to the slide button 24 such that the button 24 can be used to extend or retract the arm 18.

Figure 7:
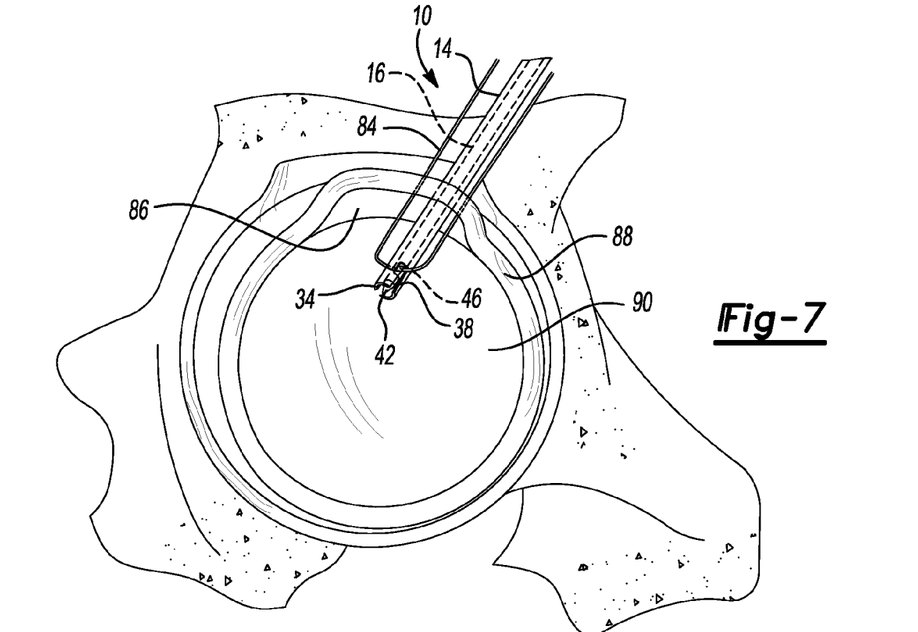
FIGS. 7 through 12 are perspective views illustrating an example method of using the suture passer device.

Referring now to FIGS. 7 through 12, an example method of using the suture passer device 10 will now be described. In FIG. 7, the inner tube 16 is retracted into the channel 36 in the outer tube 14, and a suture 84 is routed through the suture eyelet formed by the slots 38 in the outer tube 14 and the notch 46 in the inner tube 16. The suture eyelet allows the suture 84 to slide laterally through the suture eyelet while preventing the suture 84 from moving axially out of the suture eyelet. Thus, the suture 84 can be inserted into the suture eyelet while the inner tube 16 is retracted into the outer tube 14.

After the suture 84 is inserted into the suture eyelet, the distal tip 34 of the outer tube 14 can be inserted through a pre-existing separation or opening 86 between soft tissue 88 and bone 90. The opening 86 may be formed due to a tear in the soft tissue 88, and/or the opening 86 may be formed using an instrument, such as forceps, to separate the soft tissue 80 from the bone 90. Since the distal tip 34 of the outer tube 14 is blunt and the sharp distal tip 42 of the inner tube 16 is retracted within the outer tube 14, the soft tissue 88 is not damaged as the distal tip 34 is inserted through the opening 86. In one example, the soft tissue 88 is a labrum, and the bone 90 is an acetabulum or a glenoid. The soft tissue 88 may be separated from the bone 90, and the suture passer device 10 may be used to pass the suture 84 around and through the soft tissue 88 to reattach the soft tissue 88 to the bone 90.

Figure 8:
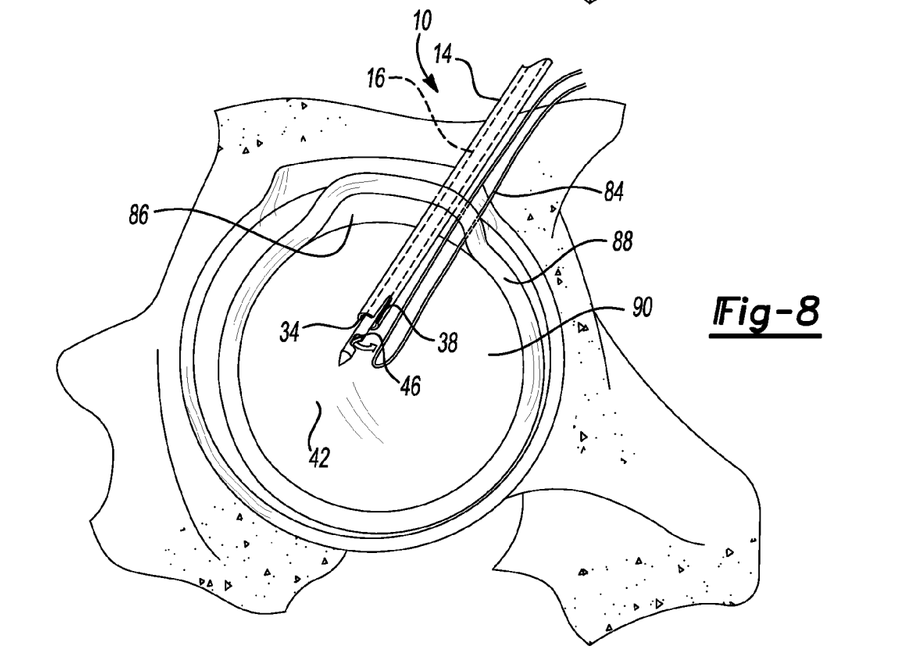

After the distal tip 34 of the outer tube 14 is inserted through the opening 86 between soft tissue 88 and bone 90, the distal tip 42 of the inner tube 16 can be extended through the distal tip 34 of the outer tube 14, as shown in FIG. 8. In turn, the suture 84 is released from the notch 46 in the inner tube 16. The distal tips 34, 42 of the outer and inner tubes 14, 16 can then be withdrawn through the opening 86 between the soft tissue 88 and the bone 90.

Figure 9:
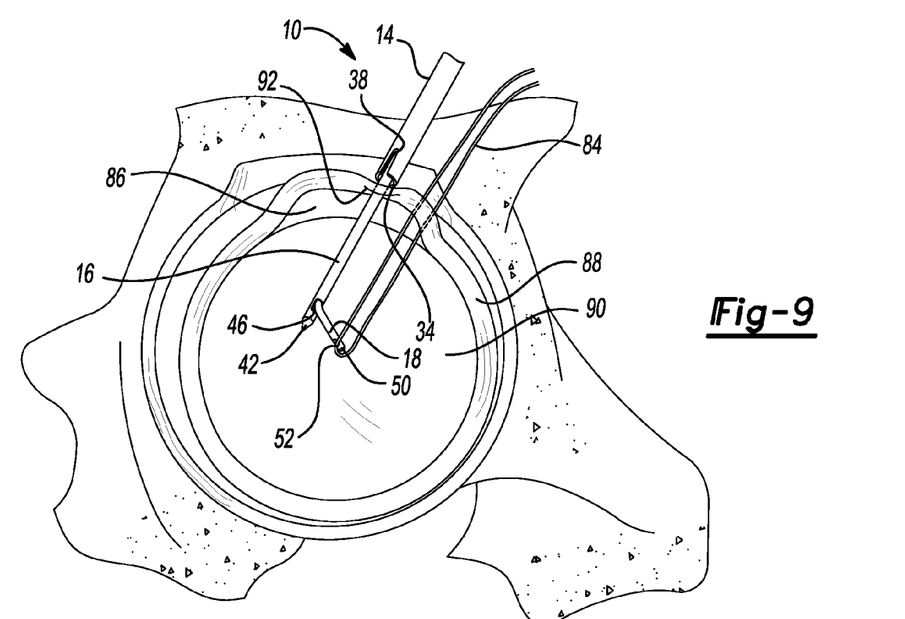

The inner tube 16 can be maintained in its extended position after the distal tips 34, 42 of the outer and inner tubes 14, 16 are withdrawn through the opening 86 between the soft tissue 88 and the bone 90. The distal tip 42 of the inner tube 16 can then be inserted through the soft tissue 88 as shown in FIG. 9, thereby piercing a hole 92 in the soft tissue 88. The flexible arm 18 can then be extended through the notch 46 in the inner tube 16 to grab or capture the suture 84 with the notch 52 in the flexible arm 18.

Figure 10:
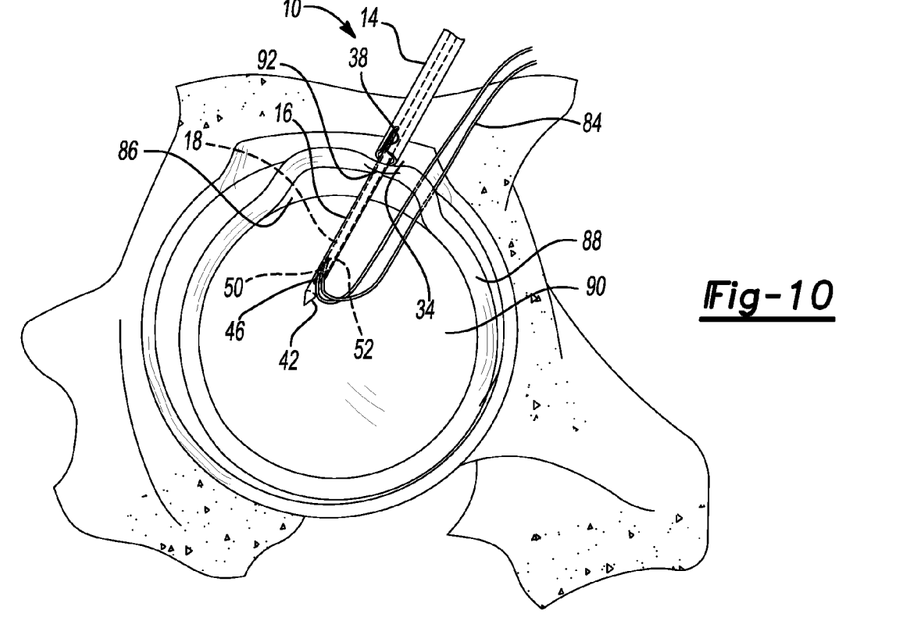
Figure 11:
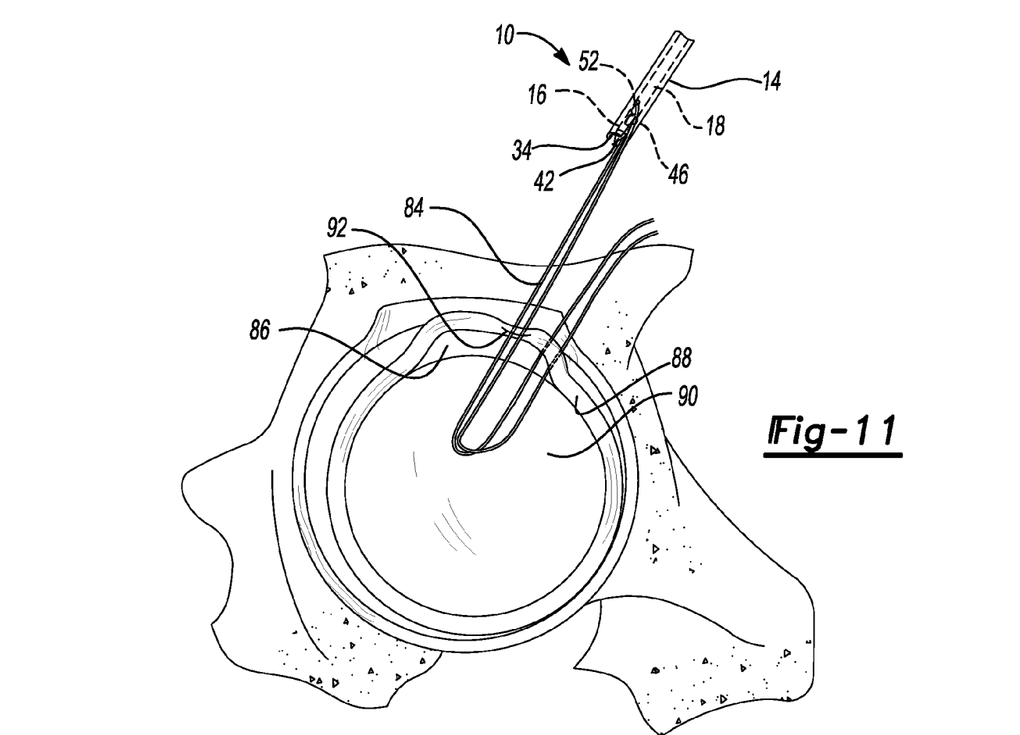

Once the suture 84 is positioned in the notch 52 in the flexible arm 18, the flexible arm 18 can be retracted into the inner tube 16 as shown in FIG. 10. When the flexible arm 18 is retracted into the inner tube 16, the suture 84 may be clamped between the inner tube 16 and the flexible arm 18 to fix the suture 84 within the inner tube 16. The inner tube 16 can then be withdrawn through the hole 92 in the soft tissue 88, as shown in FIG. 11.

Figure 12:
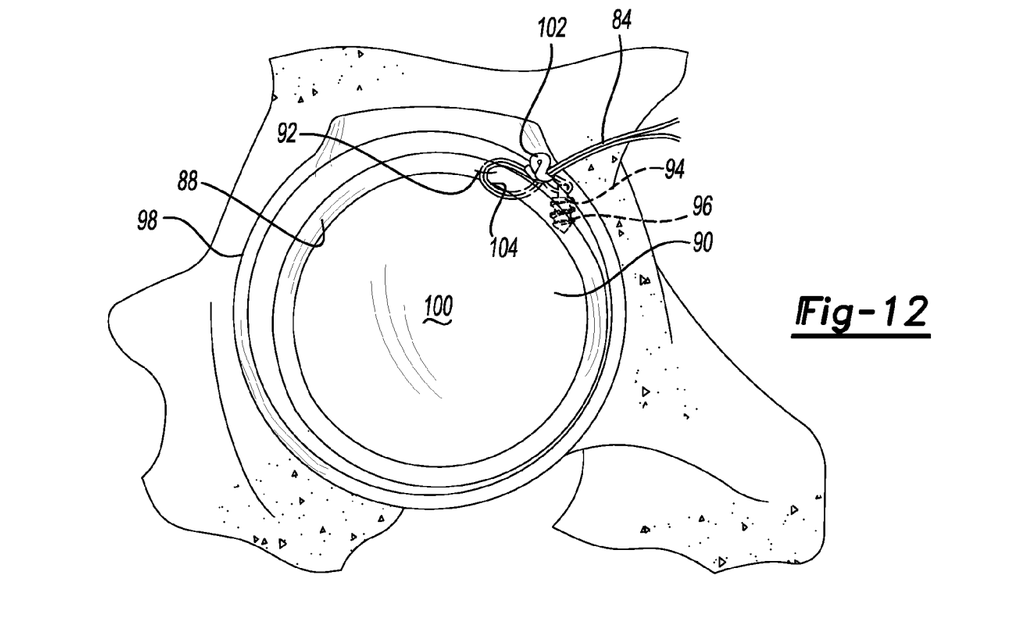

The suture 84 can then be inserted through a bone anchor 94, and the anchor 94 can be fixed within the bone 90 using, for example, threads 96 on the anchor 94, as shown in FIG. 12. The anchor 94 can be fixed to a portion 98 of the bone 90 that is remote from an articular surface 100 of the bone 90. The suture 84 can then be manipulated to form a slip knot 102 and an adjustable loop 104, and the knot 102 can be tightened to decrease the size of the adjustable loop 104 and thereby bringing the soft tissue 88 closer to the bone 90. In various implementations, the suture 84 can be inserted through the anchor 94 and/or the anchor 94 can be fixed to the bone 90 before the suture passer device 10 is used to pass the suture 84 around and through the soft tissue 88.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A suture passer device comprising:
a handle;
a shaft extending from the handle; and
a suture carrier secured to the handle and moveable through a distal end of the shaft, wherein one of the shaft and the suture carrier includes a sharp tip and the other one of the shaft and the suture carrier includes a blunt tip, wherein the suture carrier includes an inner member that defines a first notch adjacent to a distal end of the inner member and wherein, when the suture carrier is retracted into the shaft, the first notch in the inner member cooperates with a pair of slots defined in the shaft to form a suture eyelet open at both sides of the shaft and configured to permit a suture to pass through the shaft, the slots extending to and open at the distal tip of the shaft such that the shaft and the inner member are configured to deliver and release the suture from a first side of a tissue to a second side of the tissue by extending the inner member out of the shaft after the suture is on the second side of the tissue to release the suture from the first notch and the pair of slots, wherein the suture carrier includes a flexible arm axially moveable within the inner member, the flexible arm configured to extend out of the inner member and including a second notch on a distal end of the flexible arm to capture the released suture on the second side of the tissue and retract into the inner member to fix the suture within the inner member;
a trigger that is coupled to the handle, wherein applying the trigger moves the inner member through the distal end of the shaft, wherein there is a washer fixed to a proximal end of the inner member and a head on the trigger engages a surface of the washer to actuate the inner member; and
a slide button coupled to the handle that is moveable to extend and retract the flexible arm through the first notch in the inner member, wherein the flexible arm extends through a center of the washer such that the inner member and the flexible arm can each be independently actuated along the same longitudinal path.

2. The suture passer device of claim 1 wherein the shaft includes the blunt tip and the suture carrier includes the sharp tip.

3. The suture passer device of claim 1 wherein the shaft is hollow and the suture carrier extends through the shaft.

4. The suture passer device of claim 1 wherein the inner member is hollow and the flexible arm extends through the inner member.

5. The suture passer device of claim 4 wherein the shaft includes the blunt tip and at least one of the inner member and the flexible arm includes the sharp tip.

6. The suture passer device of claim 5 wherein the shaft includes a first blunt tip, the inner member includes the sharp tip, and the flexible arm includes a second blunt tip.

7. A suture passer device comprising:
- a handle;
- an outer tube extending from the handle;
- an inner tube extending through the outer tube; and
- a flexible arm extending through the inner tube;
- wherein the inner tube includes a first notch adjacent to a distal end of the inner tube and wherein, when the inner tube is retracted into the outer tube, the first notch in the inner tube cooperates with a pair of slots defined in the outer tube to form a suture eyelet open at both sides of the outer tube and configured to permit a suture to pass through the outer tube, the slots extending to and open at a distal tip of the outer tube such that the shaft and the inner tube are configured to deliver and release the suture from a first side of a tissue to a second side of the tissue by extending the inner tube out of the shaft after the suture is on the second side of the tissue to release the suture from the first notch and the pair of slots; and
- wherein the flexible arm is configured to extend out of the inner tube and including a second notch on a distal end of the flexible arm to capture the released suture on the second side of the tissue and retract back into the inner tube to fix the suture within the inner tube;
- a trigger that is coupled to the handle, wherein applying the trigger moves the inner tube through the distal end of the outer tube, wherein there is a washer fixed to a proximal end of the inner tube and a head on the trigger engages a surface of the washer to actuate the inner tube; and
- a slide button coupled to the handle that is moveable to extend and retract the flexible arm through the first notch in the inner tube, wherein the flexible arm extends through a center of the washer such that the inner tube and the flexible arm can each be independently actuated along the same longitudinal path.

8. The suture passer device of claim 7 wherein the trigger is pivotally coupled to the handle.

9. The suture passer device of claim 7 wherein the slide button is slidably coupled to the handle.

10. The suture passer device of claim 9 wherein the first notch in the inner tube defines a radial opening adjacent to a distal end of the inner tube, the slide button being moveable to extend and retract the flexible arm through the radial opening.

* * * * *